United States Patent [19]

Clitherow et al.

[11] Patent Number: 4,485,104

[45] Date of Patent: Nov. 27, 1984

[54] 1,2,4-TRIAZOLE-3-AMINES AND THEIR PHARMACEUTICAL USE

[75] Inventors: John W. Clitherow; Barry J. Price; Roger Hayes; David E. Bays, all of Hertfordshire, England

[73] Assignee: Glaxo Group Limited, London, England

[21] Appl. No.: 469,231

[22] Filed: Feb. 24, 1983

[30] Foreign Application Priority Data

Feb. 24, 1982 [GB] United Kingdom ............... 8205431

[51] Int. Cl.³ .................... A61K 31/41; C07D 403/12; C07D 403/14
[52] U.S. Cl. .............................. 424/246; 424/248.51; 424/248.54; 424/248.56; 424/263; 424/267; 424/269; 424/270; 544/60; 544/124; 544/132; 546/193; 546/194; 546/210; 548/161; 548/212; 548/266
[58] Field of Search ................. 544/60, 124, 132; 546/193, 194, 210; 548/266, 161, 212; 424/246, 248.51, 248.54, 248.56, 263, 267, 269, 270

[56] References Cited

U.S. PATENT DOCUMENTS 4,318,913  3/1982  Clitherow et al. ............... 346/210
4,323,566  4/1982  Clitherow et al. ............ 424/248.51

Primary Examiner—Robert T. Bond
Attorney, Agent, or Firm—Bacon & Thomas

[57] ABSTRACT

Compounds of the general formula (I)

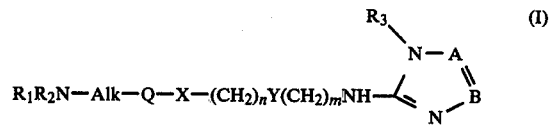

and physiologically acceptable salts, hydrates and bioprecursors thereof have been found to show pharmacological activity as selective histamine $H_2$-antagonists. The substituents in the compounds of formula (I) are defined in the main body of the disclosure.

8 Claims, No Drawings

1,2,4-TRIAZOLE-3-AMINES AND THEIR PHARMACEUTICAL USE

This invention relates to heterocyclic derivatives having action in histamine receptors, to processes for the preparation of the said heterocyclic derivatives, to pharmaceutical compositions containing the said derivatives and to the use of these derivatives in therapeutics.

Certain heterocyclic derivatives have now been found to possess potent activity as $H_2$-antagonists. These compounds, which are most particularly described below, for example show inhibition of the secretion of gastric acid when this is stimulated via histamine receptors (Ash and Schild, Brit. J. Pharmacol. Chemother, 1966, 27, 427). Their ability to do so can be demonstrated in the perfused rat stomach using the method described in British Patent Specification No. 1565966 modified by the use of sodium pentobarbitone (50 mg/kg) as anaesthetic instead of urethane, and in conscious dogs equipped with Heidenhain pouches using the methods described by Black et al, Nature 1972 236, 385. Furthermore the compounds antagonise the effect of histamine on the contraction frequency of isolated guinea pig right atrium.

Compounds with histamine $H_2$-blocking activity may be used in the treatment of conditions where there is an advantage in lowering gastric acidity, particularly in gastric and peptic ulceration, as a prophylactic measure in surgical procedures, and in the treatment of allergic and inflammatory conditions where histamine is a known mediator. Thus they may be used for example, either alone or in combination with other active ingredients in the treatment of allergic and inflammatory conditions of the skin.

The present invention provides compounds of the general formula (I)

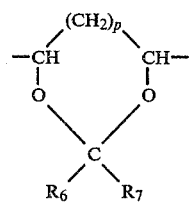

and physiologically acceptable salts, and hydrates thereof, in which $R_1$ represents hydrogen, $C_{1-14}$ alkyl, cycloalkyl, alkenyl, aralkyl, heteroalkyl, trifluoroalkyl, or alkyl substituted by hydroxy, alkoxy, amino, alkylamino, dialkylamino or cycloalkyl; and $R_2$ represents hydrogen or $C_{1-4}$ alkyl; or $R_1$ and $R_2$ may together with the nitrogen atom to which they are attached form a 5 to 10 membered ring which may be saturated or may contain at least one double bond, may be unsubstituted or may be substituted by one or more $C_{1-3}$ alkyl e.g. methyl groups or a hydroxy group and/or may contain another heteroatom selected from oxygen and sulphur;

Alk represents a straight or branched alkylene chain of 1 to 3 carbon atoms,

Q represents a furan or thiophene ring in which incorporation into the rest of the molecule is through bonds at the 2- and 5-positions, the furan or thiophene ring optionally bearing a further substituent $R_4$ adjacent to the group $R_1R_2N$—Alk—; or Q represents a thiophene ring in which incorporation into the rest of the molecule is through bonds at the 2- and 4-positions, the thiophene ring optionally bearing a further substituent $R_4$ adjacent to the group $R_1R_2NAlk$ with the proviso that when the group $R_1R_2NAlk$ is in the 4-position then the group $R_4$ is in the 5-position; or Q represents a benzene ring in which incorporation into the rest of the molecule is through bonds at the 1- and 3- or 1- and 4-positions;

$R_4$ represents halogen or $C_{1-4}$ alkyl which may be substituted by hydroxy or $C_{1-4}$ alkoxy;

X represents oxygen, sulphur, —NH—, methylene or a bond;

Y represents oxygen, sulphur, methylene or a bond;

n represents zero, 1, 2 or 3, and m is an integer from 2 to 5, with the provisos that (a) the total number of atoms in the chain $X(CH_2)_nY(CH_2)_m$ is an integer from 3 to 8, (b) when X and Y represent oxygen or sulphur then n is 2 or 3, (c) when X represents —NH— then Q is a benzene ring and Y represents methylene or a bond, and (d) when Q represents a benzene ring, X represents oxygen, and n represents 1, then m may additionally represent 1 and Y may additionally represent —CHOR$_{14}$ where $R_{14}$ represents hydrogen or acyl; and $R_3$ represents hydrogen, alkyl, alkenyl, aralkyl, or $C_{2-6}$ alkyl substituted by hydroxy or alkoxy;

either A represents N and B represents CR$_5$; or A represents CR$_5$ and B represents N; and $R_5$ represents (i) a $C_{2-6}$ straight or branched alkyl group substituted by two or three hydroxyl, alkoxy or acyloxy groups or the dihydroxyalkyl group may form a cyclic acetal or cyclic ketal structure of the formula

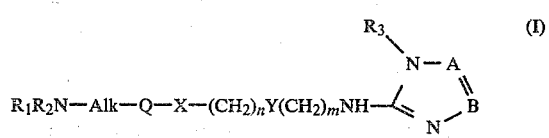

where p is zero or 1 and $R_6$ and $R_7$, which may be the same or different, each represent hydrogen, a $C_{1-4}$ alkyl group or a phenyl group; or (ii) the group $(CH_2)_qZ(CH_2)_rR_8$, where q represents an integer from 1 to 4 inclusive, r represents an integer from 1 to 6 inclusive, Z represents oxygen or sulphur and when r represents 1, $R_8$ represents the group CH=CH$_2$, alkenyl or the group COR$_9$ where $R_9$ is hydrogen, hydroxy, alkyl, aralkyl, alkoxy or the group NR$_{10}$R$_{11}$ where $R_{10}$ is hydrogen or alkyl and $R_{11}$ is hydrogen or alkyl and when r represents an integer from 2 to 6, $R_8$ has any of the meanings given above or may additionally represent hydroxy, alkoxy, aryloxy or the group NR$_{12}$R$_{13}$ where $R_{12}$ is hydrogen or alkyl and $R_{13}$ is hydrogen, alkyl, acyl, alkoxycarbonyl, alkylsulphonyl or arylsulphonyl, with the proviso that the total of q and r is preferably 6 or less; or (iii) the group $(CH_2)_xS(CH_2)_yR_{15}$, where x represents 1 or 2, y represents zero or 1, and $R_{15}$ represents a heteroaryl group.

In the above formula (I) the term "alkyl" as a group or part of a group means that the group is straight or branched and, unless otherwise stated, contains 1 to 6 carbon atoms, and in particular 1 to 4 carbon atoms, e.g. methyl or ethyl, and the term "alkenyl" means that the group has preferably 3 to 6 carbon atoms. The term "cycloalkyl" means that the group has 3 to 8 carbon atoms. The term "aryl" as a group or part of a group preferably means phenyl or substituted phenyl, for example phenyl substituted with one or more $C_{1-3}$ alkyl or $C_{1-3}$ alkoxy groups, or halogen atoms, e.g. fluorine. The term "acyl" means an aroyl, aralkanoyl or $C_{1-6}$ alkanoyl group, e.g. acetyl, formyl, phenylacetyl or benzoyl. The term "heteroaryl" as a part of a group within the definition of $R_1$ means a 5 or 6 membered monocyclic ring containing 1 to 3 heteroatoms selected from oxygen, nitrogen and sulphur, e.g. thienyl, pyridyl, furyl or thiazolyl. The heteroaryl ring may be unsubstituted or substituted by $C_{1-3}$ alkyl, $C_{1-3}$ alkoxy, hydroxy, hydroxyalkyl, aminoalkyl, alkylaminoalkyl, dialkylaminoalkyl or halogen. The alkyl portion of a heteroaralkyl group is a straight or branched $C_{1-4}$ alkyl chain, and the heteroaryl ring is linked to the alkyl portion through a carbon atom. The term "heteroaryl" within the definition of $R_{15}$ means a monocyclic or bicyclic unsaturated ring containing from 5 to 10 atoms selected from carbon, oxygen, nitrogen or sulphur. If the heteroaryl ring is monocyclic it preferably contains 5 or 6 members and if it is bicyclic it preferably contains 9 or 10 members. Examples of such heteroaryl rings are furyl, thienyl, pyrrolyl, pyridinyl, pyrimidinyl, triazinyl, oxazolyl, triazolyl, tetrazolyl, thiazolyl, thiadiazolyl, isoquinolyl, quinolyl, indolyl or benzoxazolyl. The ring structure may be unsubstituted or substituted by one or more groups selected from $C_{1-3}$ alkyl, $C_{1-3}$ alkoxy or hydroxy.

One aspect of the invention relates to compounds of formula (I) in which $R_1$, $R_2$, $R_3$, Alk, Q, X, Y, n and m are as defined above but excluding the additional possibilities for m and Y given by proviso (d), and A represents N and B represents $CR_5$ or A represents $CR_5$ and B represents N where $R_5$ is as defined in possibility (i) above or in possibility (ii) above (except that q can only represent 1 or 2).

Preferred compounds of formula (I) are those in which $R_1$ represents $C_{1-8}$ alkyl (e.g. methyl, propyl, butyl or heptyl), $C_{1-4}$ alkyl substituted by a trifluoromethyl group (e.g. 2,2,2-trifluoroethyl), $C_{2-4}$ alkyl substituted by hydroxy or a di $C_{1-3}$ alkyl amino group (e.g. 3-hydroxypropyl or dimethylaminoethyl), $C_{5-7}$ cycloalkyl (e.g. cyclohexyl), $C_{3-5}$ alkenyl (e.g. allyl), phenyl $C_{1-3}$ alkyl (e.g. benzyl), or a heteroaryl $C_{1-3}$ alkyl group where the heteroaryl ring contains one heteroatom (e.g. 2-furylmethyl);

$R_2$ represents hydrogen or methyl; or $R_1R_2N$ represents a 5-8 membered ring optionally containing a double bond, an oxygen atom or an alkyl (e.g. methyl) substituent (e.g. piperidino, morpholino, 4-methylpiperidino, pyrrolidino, hexamethylenimino or tetrahydropyridino);

Alk represents methylene;

Q represents a benzene ring incorporated into the rest of the molecule through bonds at the 1- and 3-positions; or a furan ring incorporated into the rest of the molecule through bonds at the 2- and 5-positions optionally bearing a substituent $R_4$ adjacent to the group $R_1R_2NAlk$ where $R_4$ is $C_{1-4}$ alkyl (e.g. methyl); or a thiophene ring incorporated into the rest of the molecule through bonds at the 2-and 4-positions with the substituent $R_1R_2NAlk$ in the 2-position; with the provisos that when Q is a benzene ring as just defined, then X is a bond, n is zero, Y is oxygen and m is 3, 4 or 5, or X and Y both represent oxygen and n and m are both 2, or X is oxygen, Y is CHOH and n and m are both 1; and when Q is a furan or thiophene ring as just defined, then X is a bond and either Y is sulphur or $CH_2$, n is a bond and either Y is sulphur or $CH_2$, n is 1 and m is 2, or Y is oxygen, n is 1 and m is 3;

$R_3$ represents hydrogen or alkyl (e.g. methyl);

$R_5$ represents a $C_{2-4}$ alkyl group substituted by two hydroxy groups, or a 2,2-di $C_{1-3}$ alkyl (e.g. dimethyl)-1,3-dioxolan-4-yl group or $R_5$ represents the group $(CH_2)_qZ(CH_2)_rR_8$, in which q is 1, r is 1 to 4 when Z is oxygen, or r is 1 when Z is sulphur, and $R_8$ is hydroxy, the group —CH=$CH_2$, di $C_{1-3}$ alkylamino (e.g. dimethylamino), or the group $COR_9$, where $R_9$ is $C_{1-4}$ alkoxy (e.g. ethoxy) or the group $NHR_{11}$ where $R_{11}$ is $C_{1-3}$ alkyl (e.g. methyl); or $R_5$ represents the group $(CH_2)_xS(CH_2)_yR_{15}$, in which x represents 1 and the heteroaryl group $R_{15}$ is tetrazolyl or thiadiazolyl each of which is substituted by $C_{1-3}$ alkyl (e.g. methyl), or $R_{15}$ is furyl; more preferably y is zero and $R_{15}$ is 1-methyl-1H-tetrazol-5-yl.

A particularly preferred group of compounds are those of formula (II)

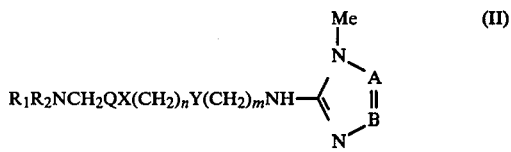

in which $R_1R_2N$ represents $diC_{1-3}$ alkylamino (e.g. dimethylamino), furylmethylamino or pyrrolidino, piperidino, 4-methylpiperidino, tetrahydropyridino or hexamethylenimino, more preferably piperidino;

A represents N and B represents $CR_5$, or A represents $CR_5$ and B represents N, where $R_5$ represents $C_{2-4}$ alkyl substituted by two hydroxy groups, 2,2,-di $C_{1-3}$ alkyl (e.g. dimethyl)-1,3-dioxolan-4-yl, (1-methyl-1H-tetrazol-5-yl)thiomethyl, or $R_5$ represents the group $CH_2Z(CH_2)_rR_8$ where, $R_8$ is hydroxy or di $C_{1-3}$alkylamino (e.g. dimethylamino), Z is oxygen and r is 4; or $R_8$ is the group —CH=$CH_2$ or the group $COR_9$ where $R_9$ is $C_{1-4}$ alkoxy (e.g. ethoxy), Z is oxygen or sulphur and r is 1; and either Q is 1,3-benzene, and X is a bond, n is zero, Y is oxygen and m is 3 or 4, more preferably 3; or X is oxygen, n is 1, Y is —CHOH— and m is 1; or Q is 2,5-furan or 2,4-thiophene, X is a bond, Y is sulphur, n is 1 and m is 2; with the proviso that $R_1R_2N$ is di $C_{1-3}$ alkylamino when Q is a furan or thiophene ring.

Particularly preferred compounds are 1-methyl-3-[[(1-methyl-1H-tetrazol-5-yl)thio]methyl]-N-[3-[3-(1-piperidinylmethyl)phenoxy]propyl]-1H-1,2,4-triazol-5-amine, 1-methyl-5-[3-[[(1-piperidinylmethyl)phenoxy]propyl]amino]-1H-1,2,4-triazole-3-ethane-1,2-diol, and their physiologically acceptable salts.

The invention includes the compounds of formula (I) in the form of physiologically acceptable salts with inorganic and organic acids. Particularly useful salts include hydrochlorides, hydrobromides, sulphates, methanesulphonates, acetates, maleates, succinates, citrates, tartrates, furmarates and benzoates. The compounds of formula (I) and their salts may also form hydrates, and the hydrates of the compounds of formula (I) are also to be considered as part of the invention. The compounds of formula (I) can exhibit tautomerism and the formulae are intended to cover all tautomers. Where optical isomers may exist the formulae are intended to cover all diastereoisomers and optical enantiomers. It should be understood that the present invention includes bioprecursors of the compounds of formula (I). The term bioprecursors means compounds which have a structure different to that of the compounds of formula (I) but which, upon administration to the animal or human being are converted in the body into a compound of formula (I).

The compounds of formula (I) preferably in the form of a salt, may be formulated for administration in any convenient way and the invention includes within its scope pharmaceutical compositions containing at least one compound according to formula (I) adapted for use in human or veterinary medicine. Such compositions may be formulated in a conventional manner using one or more pharmaceutically acceptable carriers or excipients. Such compositions may also contain if required other active ingredients e.g. $H_1$-antagonists.

Thus the compounds of formula (I) may be formulated for oral, buccal, topical, parenteral or rectal administration. Oral administration is preferred.

For oral administration, the pharmaceutical composition may take the form of for example, tablets, capsules, powders, solutions, syrups or suspensions prepared by conventional means with acceptable excipients. For buccal administration the composition may take the form of tablets or lozenges formulated in conventional manner.

The compounds of formula (I) may be formulated for parenteral administration by bolus injection or continuous infusion. Formulations for injection may be presented in unit dosage form in ampoules or in multi-dose containers, with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for reconstitution with a soluble vehicle e.g. sterile pyrogen-free water before use.

The compounds of formula (I) may also be formulated in rectal compositions such as suppositories or retention enemas, e.g. containing conventional suppository bases such as cocoa butter or other glycerides.

For topical application, the compounds of formula (I) may be formulated as ointments, creams, gels, lotions, powders or sprays in a conventional manner.

For internal administration a convenient daily dosage regime of the compounds according to the invention would be 1 to 4 doses to the total of some 5 mg to 1 g per day, preferably 5 to 500 mg per day, dependent upon the condition of the patient.

It will be appreciated that in the methods for the preparation of compounds of formula (I) given below, for certain reaction steps it may be necessary to protect various reactive substituents in the starting materials for a particular reaction and subsequently to remove the protecting group. Such protection and subsequent deprotection may be particularly pertinent where $R_1$ and $R_2$ are hydrogen atoms and/or when $R_3$ is an alkyl group bearing a hydroxy substituent and/or when $R_5$ contains a hydroxy or amino group. Standard protection and deprotection procedures can be employed, for example amines may be protected by formation of a phthalimide group which may subsequently be cleaved by treatment with a hydrazine, e.g. hydrazine hydrate or a primary amine, for example methylamine.

In describing the processes which may be used for preparing the compounds of formula (I) or intermediates useful in the preparation thereof, any of $R_1$ to $R_{15}$, A, B, Alk, Q, X, Y, Z, n, m, p, q, r, x and y in the various formulae are as defined in formula (I) unless otherwise stated.

Compounds of formula (I) in which $R_5$ represents the group $(CH_2)_qZ(CH_2)_rR_8$ or $(CH_2)_xS(CH_2)_yR_{15}$ may be prepared by reaction of a triazole of formula (I) in which $R_5$ represents the group $R_5{}^a$ where $R_5{}^a$ is $-(CH_2)_qL$ or $-(CH_2)_xL$ and L is a leaving group such as halogen, mesyloxy or tosyloxy, with an anion $\ominus Z(CH_2)_rR_8$ or $\ominus S(CH_2)_yR_{15}$. The anion may be generated from the corresponding alcohol by treatment with sodium or a strong base such as sodium hydride in the absence or presence of a solvent, for example dimethylformamide, at a temperature in the range from 20° to 120°, or from the corresponding thiol by treatment with a base such as potassium or sodium carbonate in the presence of a solvent, for example acetone, at a temperature within the above range.

The intermediates of formula (I) in which $R_5$ represents the group $R_5{}^a$ where $R_5{}^a$ is $-(CH_2)_qL$ or $-(CH_2)_xL$ may be prepared by reacting the corresponding compound in which $R_5{}^a$ is $-(CH_2)_qOH$ or $-(CH_2)_xOH$ with an acid chloride such as thionyl chloride, methanesulphonyl chloride or p-toluenesulphonyl chloride.

The intermediates of formula (I) in which $R_5$ represents the group $R_5{}^a$ where $R_5{}^a$ is $(CH_2)_qOH$ or $(CH_2)_xOH$ may be prepared as described in British Patent Specification No. 2047238A and European published specification No. 48555.

Compounds of formula (I) may also be prepared by cyclisation of an appropriate intermediate. Thus compounds of formula (I) in which $R_5$ is other than a $C_{2-6}$ straight or branched alkyl group substituted by two or three acyloxy groups, or a dihydroxyalkyl group forming a cyclic acetal or cyclic ketal structure can be prepared by cyclisation of a compound of formula (III)

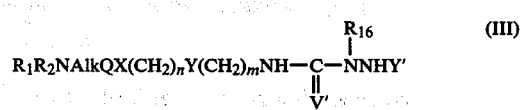
(III)

in which $R_{16}$ is a group as defined for $R_3$, V' is

and Y' is hydrogen where V is oxygen or sulphur and $R_5{}^c$ is a group as defined for $R_5$ or a group convertible thereto under the conditions of the cyclisation reaction; or V' is NH, $R_{16}$ is a group as defined for $R_3$ and Y' is

where Y'' is sulphur, oxygen or NH; or V' is sulphur or oxygen, Y' is

and $R_{16}$ is a group as defined for $R_3$; or V' is $NR_3$, $R_{16}$ is hydrogen and Y' is

where Y'' is as defined above.

Thus for example in one embodiment of the cyclisation process a compound of formula (I) in which A is N and B is the group $CR_5$ may be prepared by cyclisation of a compound of formula (IV)

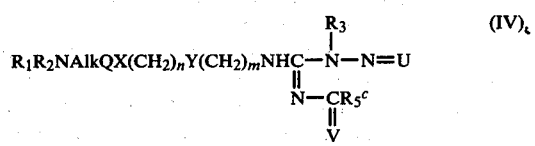

where V represents sulphur or more preferably oxygen and U represents two hydrogen atoms, in the absence or presence of a solvent, e.g. a hydrocarbon such as toluene, a ketone such as acetone, or water, and optionally with heating, for example, within the range 50° to 90°.

It may be convenient to prepare in situ compounds of formula (IV) in which U represents two hydrogen atoms by treating a compound of formula (IV) where U represents a divalent protecting group which can readily be removed to yield two hydrogen atoms, for example a benzylidene group, with an acid, e.g. hydrochloric acid, preferably with heating, and under such conditions cyclisation to give the corresponding compound of formula (I) will normally occur.

In a further embodiment of the cyclisation of compounds of formula (III), compounds of formula (I) may be prepared by cyclisation of a compound of formula (V)

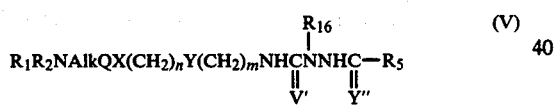

where $R_{16}$ is a group as defined for $R_3$, and either V' is NH and Y'' is sulphur, oxygen or NH, or V' is sulphur or oxygen and Y'' is NH; or $R_{16}$ is hydrogen, V' is $NR_3$ and Y'' is sulphur.

When Y'' represents sulphur then tautomerism with the adjacent NH group is possible (i.e.

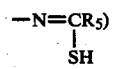

and the —SH group may be alkylated under standard conditions. The S-alkylated compound may also be used in the cyclisation process.

The cyclisation may be carried out by heating the compound (V) (e.g. within the range 80° to 150°) in the absence or presence of a solvent (e.g. acetonitrile or dimethylformamide), or under basic conditions (e.g. using aqueous potassium hydroxide).

In a convenient embodiment of this process an intermediate of formula (V) in which $R_{16}$ is a group as defined for $R_3$, V' is NH and Y'' is oxygen; or $R_{16}$ is hydrogen, V' is $NR_3$ and Y'' is oxygen may be prepared in situ by the reaction of an aminoguanidine (VI)

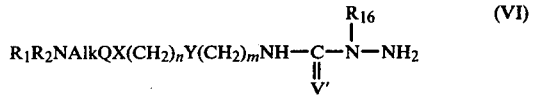

with an acid $R_5COOH$ or with an activated derivative thereof. Suitable activated derivatives include acid halides, e.g. acid chlorides, alkylchloroformates, acid anhydrides including mixed anhydrides (e.g. acetic formic anhydride), esters such as alkyl esters, ortho esters (such as trialkylorthoesters, e.g. $R_5C(OEt)_3$) and (1-alkyl-2-pyridinyl) esters, or derivatives formed from a coupling agent such as carbonyldiimidazole or a carbodiimide such as dicyclohexylcarbodiimide.

The acid and the aminoguanidine (VI) may be heated together, under which conditions cyclisation of the intermediate (V) takes place directly to give a compound of formula (I). In the case of an activated derivative, an aprotic solvent, e.g. tetrahydrofuran may be used at temperatures from ambient to reflux. When using an acyl chloride as the activated derivative the reaction may also be carried out in the presence of a base, e.g. a tertiary amine such as pyridine, which may also be used as the solvent.

In general intermediates of formula (IV) may be prepared from the appropriate diamines by methods analogous to those described in British Patent Specification No. 2047238A, and intermediates of formula (V) may be prepared from the appropriate diamines by methods analogous to those described in British Patent Specification No. 2023133A and in European Patent Specification No. 48555. The aminoguanidines (VI) may be prepared as described in British Patent Specification No. 2023133A, and European Patent Specification No. 48555.

Compounds of formula (I) in which Alk is $CH_2$ may be prepared by treating an aldehyde of formula (VII)

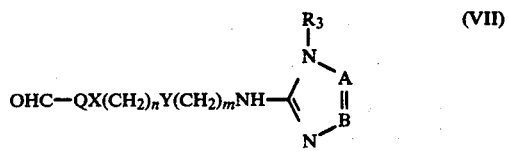

with an amine $R_1R_2NH$, for example in a solvent such as tetrahydrofuran or an alkanol, e.g. ethanol, followed by reduction using for example a hydride reducing agent such as an alkali or alkaline earth metal borohydride, e.g. sodium borohydride or lithium aluminium hydride, or hydrogen and a metal catalyst such as palladium or platinum. The reactions may be carried out at a temperature of 0° to 80° C.

The intermediates of formula (VII) may be prepared from compounds of formula (VIII)

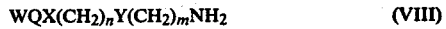

in which W represents a protected aldehyde group, e.g. a cyclic acetal such as an ethylene acetal, by methods analogous to those described herein for preparing compounds of formula (I) from the appropriate diamine.

Compounds of formula (I) in which $R_5$ has one meaning may be converted into compounds of formula (I) in which $R_5$ has another meaning using standard methods of interconversion.

Thus, compounds in which $R_5$ represents a $C_{2-6}$ straight or branched alkyl group substituted by two or three acyloxy groups, or Y represents $CHOR_{14}$ where $R_{14}$ is acyl, may be prepared by reacting the corresponding alcohol with an activated derivative (e.g. an acid chloride or an acid anhydride) of an appropriate acid. The reaction may be carried out at room temperature, optionally in the presence of a solvent (e.g. pyridine, tetrahydrofuran, acetone or dimethylformamide), and preferably in the presence of a base (e.g. pyridine, triethylamine or an alkali metal carbonate such as potassium carbonate).

Compounds in which $R_5$ represents a $C_{2-6}$ straight or branched alkyl group substituted by tow or three alkoxy groups may be prepared from the corresponding alcohol by treatment with an halogenating agent, for example thionyl chloride, followed by reaction of the resulting halocompound with an appropriate alkanol in the presence of sodium at a temperature within the range 20°–50°. Alternatively the intermediate halocompound may be treated with an appropriate alkanol in a solvent such as dimethylformamide, in the presence of a strong base such as sodium hydride, at a temperature within the range 20°–100°.

Compounds in which $R_5$ represents the group $(CH_2)_qZ(CH_2)_rR_8$ where $R_8$ is $NR_{12}R_{13}$ and $R_{12}$ and $R_{13}$ each represent hydrogen or alkyl may be prepared from the corresponding alcohol in which $R_8$ is hydroxy by treatment with a reagent capable of converting the group $R_8$ into a leaving group, for example thionyl chloride, followed by reaction of the resulting compound of formula (I) in which $R_5$ represents $(CH_2)_qZ(CH_2)_rL$ where L is a leaving group e.g. halogen with ammonia or an appropriate amine $R_{12}R_{13}NH$ preferably in a solvent such as an alkanol, e.g. ethanol at a temperature within the range 80°–120°.

Compounds in which $R_8$ is the group $NHR_{12}$ may be converted into compounds in which $R_8$ is the group $NR_{12}R_{13}$ where $R_{13}$ is either an acyl group or an aryl- or alkylsulphonyl group, by reaction with an activated derivative of the appropriate carboxylic or sulphonic acid.

Suitable activated derivatives include acid halides, e.g. acid chlorides, alkylchloroformates, acid anhydrides including mixed anhydrides (e.g. acetic formic anhydride), and esters such as alkyl esters and ortho esters.

The reaction with an acid halide is preferably carried out in the presence of a base, e.g. an inorganic base such as sodium hydroxide or an organic base such as triethylamine or pyridine. The reaction with an alkylchloroformate is preferably carried out in the presence of a base, e.g. potassium carbonate or triethylamine, in a solvent such as dimethylformamide. The reaction with an acid anhydride is carried out in the absence or presence of a solvent such as pyridine.

Compounds in which $R_8$ is the group $-CONR_{10}R_{11}$ may be prepared by reacting an activated derivative of the corresponding carboxylic acid in which $R_8$ is the group $-CO_2H$, e.g. an ester with ammonia or an appropriate amine $HNR_{10}R_{11}$ in a suitable solvent (e.g. an alcohol such as ethanol) at a temperature of from 20° C. to 120° C.

Compounds in which $R_5$ includes the group

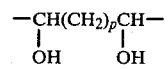

may be converted into the corresponding compounds in which $R_5$ includes the group

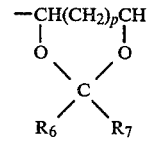

by reaction with an aldehyde or ketone $R_6R_7CO$, e.g. acetone in the presence of an acid, e.g. p-toluenesulphonic acid. The reaction is carried out in the absence or presence of a solvent, e.g. benzene, at a temperature between room temperature and reflux.

Where the product of any of the above processes is a free base and an acid addition salt, in particular a physiologically acceptable salt is required, the salt may be formed in conventional manner. Thus, for example, a generally convenient method of forming the salts is to mix appropriate quantities of the free base and the acid in an appropriate solvent(s) e.g. an alcohol such as ethanol or an ester such as ethyl acetate. The invention also includes interconversion of one salt of the compound of formula (I) into another.

The invention is illustrated but not limited by the following Examples and Preparations, in which temperatures are in °C.

Unless otherwise stated the silica used for column chromatography was Merck Kieselgel 60 (7734).

T.l.c. refers to thin layer chromatography and this and preparative chromatography were carried out on silica using, unless otherwise stated, one of the following solvent systems:

System A: Dichloromethane:ethanol:0.88 ammonia (50:8:1)

System B: Dichloromethane:ethanol:0.88 ammonia (25:8:1)

System C: Dichloromethane:ethanol:0.88 ammonia (100:8:1)

System D: Ethyl acetate:isopropanol:water:0.88 ammonia (25:15:8:2)

System E: Dichloromethane:ethanol:0.88 ammonia (75:8:1)

PREPARATION

Methyl N-[2,3-diacetyloxypropionyl]-1-methyl-2-(phenylmethylene)hydrazine carboximidothioate Di-acetyl glyceric acid (13.8 g) was heated under reflux in thionyl chloride (50 ml) for 4 h. The solution was evaporated in vacuo and azeotroped with toluene (3×50 ml) to give an oil which was used without further purification. This oil was dissolved in dichloromethane (100 ml) and added dropwise to a solution of methyl 1-methyl-2-(phenylmethylene)hydrazine carboximidothioate hydrochloride (15.4 g) in dichloromethane (250 ml) and triethylamine (19.3 ml) which had previously been stirred at 20° for 0.5 h. The reaction was stirred at 20° for 15 h before adding water. The organic phase was separated, dried (MgSO₄) and evaporated to leave a residue (7 g) which was chromatographed using ether as eluent to give the title compound as a yellow waxy solid (4.6 g).

NMR (CDCl$_3$): 2.16, s, (1H); 2.2–2.7. m, (3H); 4.58–5.45, m, (3H); 6.57, s, (3H); 7.67, s, (3H); 7.85, s, (3H); 7.93, s, (3H).

EXAMPLE 1

1-Methyl-5-[3-[[(1-piperidinylmethyl)phenoxy]propyl]amino]-1H-1,2,4-triazole-3-ethane-1,2-diol, hemicitrate To a mixture of methyl N-[2,3-diacetyloxypropionyl]-1-methyl-2-(phenylmethylene)hydrazine carboximidothioate (2.69 g) in toluene (100 ml) was added 3-[3-(1-piperidinylmethyl)phenoxy]propanamine (1.5 g) and the resulting solutions stirred at 20° for 16 h before 5N hydrochloric acid (25 ml) was added and the two phase mixture stirred vigorously for a further 16 h. The acidic layer was separated and the toluene layer washed with 2N hydrochloric acid. The combined acidic layers were washed with toluene before being basified and subsequently saturated with solid sodium carbonate. The basic solution was extracted with ethyl acetate and the combined organic extracts dried (MgSO$_4$) and evaporated. The residue (2.0 g) was chromatographed using chloroform: methanol (5:1) as eluent to give a foam (0.6 g). The foam was dissolved in ethyl acetate (20 ml) with the aid of methanol (4 ml) and treated with a stoichiometric amount of citric acid in ethyl acetate (20 ml), under nitrogen. The suspension was stirred 20° for 0.5 h, the compound was collected and dried in vacuo to give the title compound as a white solid (0.53 g), m.p. 73°–74° softens:

T.l.c. System D. Rf. 0.46.

EXAMPLE 2

(a)

1-Methyl-N-[3-[3-(1-piperidinylmethyl)phenoxy]propyl]-3-[(2-propenyloxy)methyl]-1H-1,2,4-triazol-5-amine 1-Methyl-5-[[3-[3-(1-piperidinylmethyl)phenoxy]propyl]amino]-1H-1,2,4-triazole-3-methanol (3.59 g) was dissolved in thionyl chloride (10 ml) and heated at reflux for 15 min. The orange solution was evaporated under reduced pressure to leave a gum which was stirred in water (35 ml) at 20°. Sodium bicarbonate and sodium carbonate (3 g) were added, and the suspension was stirred with ethyl acetate. The organic phase was separated, dried for 1 h with sodium carbonate and evaporated in vacuo to give an oil. This oil was dissolved in allyl alcohol (10 ml) and added to a solution of sodium (0.3 g) in allyl alcohol (8 ml). The reaction mixture was heated on a steam-bath for 6 h, poured into water and extracted with ethyl acetate. The organic phase was extracted with 2N hydrochloric acid. The acidic extract was basified to pH 9 with potassium carbonate and extracted with ethyl acetate. Evaporation of the organic extracts gave an oil (1.1 g) which was chromatographed using dichloromethane:ethanol:ammonia: (70:8:1) as eluent to give the title compound as an oil (0.4 g)

Assay Found: C, 65.64; H, 8.46; N, 17.44. C$_{22}$H$_{33}$N$_5$O$_2$ requires: C, 66.14; H, 8.33; N, 17.53.

T.l.c. System C Rf 0.4.

(b) Similarly prepared by this procedure from 1-methyl-5-[[3-[3-(1-piperidinylmethyl)phenoxy]propyl]amino]-1H-1,2,4-triazole-3-methanol (3.59 g) and thionyl chloride (10 ml), followed by addition of a solution of sodium (0.3 g) in butane-1,4-diol (10 g) was 4-[1-methyl-5-[[3-[3-(1-piperidinylmethyl)phenoxy]propyl]amino-1H-1,2,4-triazol-3-yl]methoxy]butanol compound with ethanol (2:1) (0.87 g).

Assay Found: C, 63.12; H. 8.81; N, 15.56. C$_{23}$H$_{27}$N$_5$O$_3$·½C$_2$H$_5$OH requires: C, 63.40; H, 8.87; N, 15.41.

NMR (CDCl$_3$): 2.8, t, (1H); 3.0–3.3, m, (3H); 5.4, br.t, (1H); 5.62, s, (2H); 5.95, t, (2H); 6.4, m, (6H); 6.5, s, (3H); 6.6, s, (2H); 7.0, br, (1H); 7.6, m, (4H); 7.9, m, (2H); 8.1–8.7, m, (10H).

EXAMPLE 3(a)

Ethyl [[[1-Methyl-5-[[3-[3-(1-piperidinylmethyl)phenoxy]propyl]amino]-1H-1,2,4-triazol-3-yl]methyl]thio]acetate hemihydrate 1-Methyl-5-[[3-[3-(1-piperidinylmethyl)phenoxy]propyl]amino]-1H-1,2,4-triazole-3-methanol, compound B, (7.2 g) was dissolved in thionyl chloride (30 ml) at 20° and heated under reflux for 15 min. The cooled solution was evaporated in vacuo and the oil dissolved in water (30 ml), cautiously basified with solid sodium bicarbonate, sodium carbonate (3 g) added, and the mixture extracted with ethyl acetate. The extract was dried (Na$_2$CO$_3$, 1 h) and evaporated to give on oil.

The resulting oil was dissolved in acetone (100 ml) and heated under reflux for 16 h with anhydrous potassium carbonate (2.76 g) and ethyl mercaptoacetate (2.4 g). The mixture was partitioned between aqueous potassium carbonate and ethyl acetate. The ethyl acetate extract was dried and evaporated and the residue (5.1 g) was chromatographed using System E as eluent to give the title compound (2.9 g) as a pale yellow oil.

Found: C, 58.7; H, 7.6; N, 14.8. C$_{25}$H$_{35}$N$_5$O$_3$S.½H$_2$O requires: C, 58,7; H, 7.7; N, 14.9%.

N.m.r. (CDCl$_3$): 2.75, dd, (1H); 3–3.33, m, (3H); 5.45, t, (1H); 5.66–6, q+t, (4H); 6.23–6.7, s+s+q+s+s, (11H); 7.61–7.86, m, (6H); 8.45, m, (6H); 8.7, t, (3H).

The following compounds were similarly prepared from the compound B and the appropriate starting materials.

3(b) Compound B (1.41 g), 5-mercapto-1-methyltetrazole (0.506 g) and potassium carbonate (0.54 g) with the exceptions that the mixture was chromatographed using System C to give an oil (1.0 g) which was dissolved in ethyl acetate and treated with excess ethereal hydrochloric acid, gave 1-methyl-3-[[(1-methyl-1H-tetrazol-5-yl)thio[methyl]-N-[3-[3-(1-piperidinylmethyl)phenoxy]propyl]-1H-1,2,4-triazol-5-amine dihydrochloride sesquihydrate (0.6 g) as a white powder m.p. slowly softens above 40°.

N.m.r. (D$_2$O): 2.6, 2.9–3.0, m, (4H); 5.7–5.9, m, (6H), 6.04, s, (3H): 6.4–6.6, s+m, (7H); 7.05, t, (2H); 7.9–8.6, m, (8H).

3(c) Compound B (1.41 g), 2-mercapto-5-methyl-1,3,4-thiadiazole (0.52 g) and potassium carbonate (0.54 g), with the exception that the mixture was chromatographed using System C, gave 1-methyl-3-[[(5-methyl-1,3,4-thiadiazol-2-yl)thio]methyl]-N-[3-[3-(1-piperidinylmethyl)phenoxy]propyl]-1H-1,2,4-triazol-5-amine (0.62 g) as a white powder m.p. 63° softens melts 72°–74°, Found: C, 55.9; H. 6.7; N, 20.7. C$_{22}$H$_{31}$N$_7$OS$_2$ requires: C, 55.8; H, 6.6; N, 20.7%.

EXAMPLE 4

3-[[4-(Dimethylamino)butoxy]methyl]-1-methyl-N-[3-[3-(1-piperidinylmethyl)phenoxy]propyl]-1H-1,2,4-triazole-5-amine 4-[[1-Methyl-5-[[3-[3-(1-piperidinylmethyl)phenoxy]propyl]amino]-1H-1,2,4-triazol-3-yl]methoxy]butanol (0.5 g) was dissolved in thionyl chloride (10 ml) and stirred at 20° for 1.5 h. The solution was evaporated in vacuo and the residue dissolved in water (20 ml), basified with solid sodium bicarbonate and sodium carbonate (~2 g). The mixture was extracted with ethyl acetate, the extract dried (Na$_2$CO$_3$, 1h), evaporated and the residual oil was dissolved in ethanolic dimethylamine (33%, 15 ml) and the solution was heated in an autoclave at 80° for 8 h. The solution was evaporated and the residual oil (0.3 g) was chromatographed using System A as eluent to give the title compound (0.2 g) as a pale yellow oil.

N.m.r. (CDCl$_3$): 1.74, dd, (1H); 3–3.32, m, (3H); 5.48, t, (1H); 5.58, s, (2H); 5.86, t, (2H); 6.24–6.64, s+s+m, (9H); 7.48–8, m+s, (14H); 8.21–8.68, m, (10H).

T.l.c. System B Rf 0.55.

EXAMPLE 5

3-(2,2-Dimethyl-1,3-dioxolan-4-yl)-1-methyl-N-[3-[3-(1-piperidinylmethyl-phenoxy]propyl]-1H-1,2,4-triazol-5-amine A solution of 1-methyl-5-[[3-[3-(1-piperidinylmethyl)phenoxy]propyl]amino]-1H-1,2,4-triazole-3-ethane-1,2-diol (0.08 g), 2,2-dimethoxypropane (2.0 ml) and 4-toluenesulphonic acid (0.03 g) in acetone (10 ml) was stirred at 20° for 16 h, evaporated and partitioned between 2N sodium carbonate and ethyl acetate. The ethyl acetate extract was dried and evaporated and the resulting oil (0.07 g) was chromatographed using System E as eluent to give the title compound (0.025 g) as an amber gum.

N.m.r. (CDCl$_3$): 2.78, t, (1H); 3.08–3.23, m, (3H); 4.96, dd, (1H); 5.48, t, (1H); 5.72, dd, (1H); 5.80, t, (1H); 5.88, t, (2H); 6.37, q, (2H); 6.46, s, (3H); 6.55, s, (2H); 7.62, m, (4H); 7.87, m, (2H); 8.4–8.6, m, (9H).

T.l.c. System D Rf 0.7.

EXAMPLE 6

N-Methyl [[[1-methyl-5-[[3-[3-(1-piperidinylmethyl)phenoxy]propyl]amino]-1H-1,2,4-triazol-3-yl]methyl]thio]acetamide A solution of ethyl [[[1-methyl-5-[[3-[3-(1-piperidinylmethyl)phenoxy]propyl]amino]-1H-1,2,4-triazol-3-yl]methyl]thio]acetate (0.4 g) in ethanolic methylamine (33%, 20 ml) under nitrogen, was heated under reflux for 30 h, cooled, evaporated in vacuo, the residue dissolved in 2N hydrochloric acid (20 ml), and washed with ethyl acetate. The acidic layer was basified with potassium carbonate extracted with ethyl acetate and the extract was dried and evaporated to give an oil (0.28 g) which was chromatographed using System E as eluent to give the title compound (0.13 g) as an oil.

N.m.r. (CDCl$_3$) : 2.46, s(br), (1H); 2.79, t, (1H); 3.07, m, (2H); 3.22, dd, (1H); 5.34, t, (1H); 5.85, t, (2H); 6.4, s+q, (4H); 6.46, s, (3H); 6.56, s, (2H); 6.72, s, (2H); 7.19, d, (3H); 7.63, m, (4H); 7.86, m, (2H); 8.42, m, (4H); 8.57, m, (2H).

T.l.c. System A, Rf 0.7.

EXAMPLE 7

3-[[[(2-Furanyl)methyl]thio]methyl]-1-methyl-N[3-[3-(1-piperidinylmethyl)phenoxy]propyl]-1H-1,2,4-triazol-5-amine A solution of 1-methyl-5-[[3-[3-(1-piperidinylmethyl)phenoxy]propyl]amino]-1H-1,2,4-triazole-3-methanol (3.59 g) in thionyl chloride (10 ml) was heated on a steam bath for 10 min. The solution was evaporated to dryness and the residue was dissolved in water. Sodium bicarbonate was added to the solution until no more effervescence occurred. Sodium carbonate (3 g) was added, and the suspension was extracted with ethyl acetate. The organic extract was dried and evaporated to give a brown oil (4.1 g).

A portion of this oil (3.2 g) was dissolved in absolute ethanol (40 ml) and added dropwise at 5° to a solution of furfurylmercaptan (1.14 g) and sodium (0.34 g) in absolute ethanol (20 ml). The suspension was allowed to stand at room temperature for 18 h, filtered, and the filtrate was evaporated to dryness. The residue was dissolved in 0.2N hydrochloric acid, washed with ethyl acetate, and basified with excess solid sodium carbonate. The basic solution was extracted with ethyl acetate. The organic extract was dried and evaporated to give an oil (2.2 g) which was purified by column chromatography using chloroform as eluent to give the title compound as an oil (1.2 g).

T.l.c. System C Rf 0.45.

N.m.r. (CDCl$_3$) 2.7, d, (1H); 2.8, t, (1H); 3.0–3.4, m, (3H); 3.8, m, (2H); 5.5, t, (1H); 5.95, t, (2H); 6.25, s, (2H); 6.3–6.7, m, (9H); 7.5–8.1, m, (6H); 8.5, m, (6H).

EXAMPLES OF PHARMACEUTICAL COMPOSITIONS

Tablets

|  | mg/tablet |
| --- | --- |
| Active ingredient | 5.0 to 125.0 |
| Microcrystalline Cellulose USP | 293.5 to 173.5 |
| Magnesium Stearate BP | 1.5 |
| Compression weight | 300.0 |

The drug is sieved through a 250 μm sieve, blended with the excipients and compressed using 9 mm diameter punches. Other strengths may be prepared by altering the compression weight and using punches to suit.

The tablets may be film coated using suitable film forming polymers such as hydroxypropyl methyl cellulose using standard techniques. Alternatively the tablets may be sugar coated.

Capsules

|  | mg/capsule |
| --- | --- |
| Active ingredient | 5.0 to 125.0 |
| Starch 1500* (USP) | 243.5 to 123.5 |
| Magnesium Stearate BP | 1.5 |
| Fill weight | 250.0 |

*A form of directly compressible starch

The active ingredient is sieved through a 250 μm sieve and blended with the excipients. The mix is filled into No. 2 hard gelatin capsules using suitable machinery. Other doses may be prepared by altering the fill weight, and, if necessary, changing the capsule size.

Injection for Intravenous Administration

|  | % w/v |
| --- | --- |
| Active ingredient | 0.20 to 0.50 |
| Water for Injection B.P to | 100.0 |

Sodium chloride may be added to adjust the tonicity of the solution and the pH may be adjusted to that of maximum stability using either dilute acid or alkali. The solution is prepared, clarified and filled under nitrogen, or other inert gas, into appropriate sized ampoules sealed by the fusion of glass. The injection is sterilised by heating in an autoclave using one of the acceptable cycles. Alternatively the solution may be sterilised by filtration and filled into sterile ampoules under aseptic conditions.

Syrup

|  | mg/5 ml dose |
| --- | --- |
| Active ingredient | 5.0 to 250.0 |
| Sucrose | 2795.0 to 2550.0 |
| Glycerine | 500.0 |
| Buffer<br>Flavour } as necessary<br>Colour |  |
| Distilled water to | 5.0 ml |

The active ingredient, buffer, flavour, preservative and colour are dissolved in some of the water. The remainder of the water is heated to approximately 80° C. and the sucrose is dissolved in this water and cooled. The two solutions are mixed, adjusted to volume and clarified by filtration. Alternatively, the active ingredient, sucrose, buffer, flavour, colour and preservative may be mixed and the powder filled into bottles for later reconstitution by the addition of water.

We claim:

1. A compound of formula (I)

$$R_1R_2N-Alk-Q-X-(CH_2)_nY(CH_2)_mNH- \underset{N}{\overset{N-A}{\diagdown}}B \quad (I)$$

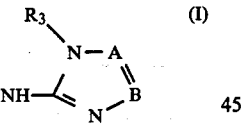

or a physiologically acceptable salt or hydrate thereof, in which $R_1$ represents hydrogen, $C_{1-14}$ alkyl, $C_{3-8}$ cycloalkyl, $C_{3-6}$ alkenyl, ar $C_{1-6}$ alkyl, wherein the ar portion is phenyl or phenyl substituted with one or more $C_{1-3}$ alkyl or $C_{1-3}$ alkoxy groups or halogen atoms; heteroarylalkyl, wherein the heteroaryl portion is thienyl, pyridyl, furyl or thiazolyl the heteroaryl ring may be unsubstituted or substituted by $C_{1-3}$ alkyl, $C_{1-3}$ alkoxy, hydroxy, hydroxy $C_{1-6}$ alkyl, amino $C_{1-6}$ alkyl, $C_{1-6}$ alkylamino $C_{1-6}$ alkyl, di-$C_{1-6}$ alkylamino-$C_{1-6}$ alkyl or halogen, and the alkyl portion of the heteroaralkyl group is a straight or branched $C_{1-4}$ alkyl chain, and the heteroaryl ring is linked to the alkyl portion through a carbon atom; trifluoro $C_{1-6}$ alkyl or $C_{1-6}$ alkyl substituted by hydroxy, $C_{1-6}$ alkoxy, amino, $C_{1-6}$ alkylamino, di-$C_{1-6}$ alkylamino or $C_{3-8}$ cycloalkyl; and $R_2$ represents hydrogen or $C_{1-4}$ alkyl; or $R_1$ and $R_2$ may together with the nitrogen atom to which they are attached form piperidino, morpholino, 4-$C_{1-6}$alkyl-piperidino, pyrrolidino, hexamethyleneiminoor tetrahydropyridino;

Alk represents a straight or branched alkylene chain of 1 to 3 carbon atoms,

Q represents a furan or thiophene ring in which incorporation into the rest of the molecule is through bonds at the 2- and 5-positions, the furan or thiophene ring optionally bearing a further substituent $R_4$ adjacent to the group $R_1R_2N$-Alk-; or Q represents a thiophene ring in which incorporation into the rest of the molecule is through bonds at the 2- and 4-positions, the thiophene ring optionally bearing a further substituent $R_4$ adjacent to the group $R_1R_2NAlk$ with the proviso that when the group $R_1R_2NAlk$ is in the 4-position then the group $R_4$ is in the 5-position; or Q represents a benzene ring in which incorporation into the rest of the molecule is through bonds at the 1- and 3- or 1- and 4-positions;

$R_4$ represents halogen or $C_{1-4}$ alkyl which may be substituted by hydroxy or $C_{1-4}$ alkoxy;

X represents oxygen, sulphur, —NH—, methylene or a bond;

Y represents oxygen, sulphur, methylene or a bond;

n represents zero, 1, 2 or 3, and m is an integer from 2 to 5, with the provisos that (a) the total number of atoms in the chain $X(CH_2)_nY(CH_2)_m$ is an integer from 3 to 8, (b) when X and Y represent oxygen or sulphur then n is 2 or 3, (c) when X represents —NH— then Q is a benzene ring and Y represents methylene or a bond, and (d) when Q represents a benzene ring, X represents oxygen, and n represents 1, then m may additionally represent 1 and Y may additionally represent —$CHOR_{14}$ where $R_{14}$ represents hydrogen, aroyl, ar $C_{2-7}$ alkanoyl or $C_{1-6}$ alkanoyl, wherein the ar portion is as defined above; and $R_3$ represents hydrogen, $C_{1-6}$ alkyl, $C_{3-6}$ alkenyl, ar $C_{1-6}$ alkyl, wherein the ar portion is as defined above, or $C_{2-6}$ alkyl substituted by hydroxy or $C_{1-6}$ alkoxy;

either A represents N and B represents $CR_5$; or A represents $CR_5$ and B represents N; and $R_5$ represents (i) a $C_{2-6}$ straight or branched alkyl group substituted by two or three hydroxyl, $C_{1-6}$ alkoxy or acyloxy groups where the acyl portion is aroyl, ar $C_{2-7}$ alkanoyl or $C_{1-6}$ alkanoyl, wherein ar is as defined above, or the dihydroxyalkyl group may form a cyclic acetal or cyclic ketal structure of the formula

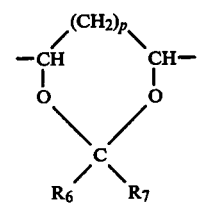

where p is zero or 1 and $R_6$ and $R_7$, which may be the same or different, each represents hydrogen, a $C_{1-4}$ alkyl group or a phenyl group; or (ii) the group $(CH_2)_qZ(CH_2)_rR_8$, where q represents an integer from 1 to 4 inclusive, r represents an integer from 1 to 6 inclusive, Z represents oxygen or sulphur and when r represents 1, $R_8$ represents the group $CH=CH_2$, $C_{3-6}$ alkenyl or the group $COR_9$ where $R_9$ is hydrogen, hydroxy, $C_{1-6}$ alkyl, ar $C_{1-6}$ alkyl wherein ar is as defined above, $C_{1-6}$ alkoxy or the group $NR_{10}R_{11}$ where $R_{10}$ is hydrogen or $C_{1-6}$ alkyl and $R_{11}$ is hydrogen or $C_{1-6}$ alkyl and when r represents an integer from 2 to 6, $R_8$ has any of the meanings given above or may additionally represent hydroxy, $C_{1-6}$ alkoxy, aryloxy wherein ar is as defined above or the group $NR_{12}R_{13}$ where $R_{12}$ is hydrogen or $C_{1-6}$ alkyl and $R_{13}$ is hydrogen, $C_{1-6}$ alkyl, aroyl, ar $C_{1-6}$ alkanoyl wherein ar is as defined above; $C_{1-6}$ alkanoyl, $C_{1-6}$ alkoxycarbonyl, $C_{1-6}$ alkylsulphonyl or arylsulphonyl where ar is as defined above; or (iii) the group $(CH_2)_xS(CH_2)_yR_{15}$, where x represents 1 or 2, y represents zero or 1, and $R_{15}$ represents a heteroaryl group which is furyl, thienyl, pyrroyl, pyridinyl, pyrimidinyl, triazinyl, oxazolyl, triazolyl, thiadiazoyl, isoquinolyl, quinolyl, indolyl or benzoxazolyl, and with the ring(s) unsubstituted or substituted by one or more $C_{1-3}$ alkyl, $C_{1-3}$ alkoxy or hydroxy groups.

2. A compound as claimed in claim 1 in which:

$R_1$ represents $C_{1-8}$ alkyl, $C_{1-4}$ alkyl substituted by a trifluoromethyl group, $C_{2-4}$ alkyl substituted by hydroxy or a di $C_{1-3}$ alkyl amino group, $C_{5-7}$ cycloalkyl, $C_{3-5}$ alkenyl, phenyl $C_{1-3}$ alkyl, or a heteroaryl $C_{1-3}$ alkyl group where the heteroaryl portion is thienyl, pyridyl or furyl;

$R_2$ represents hydrogen or methyl; or $R_1R_2N$ represents piperidino, morpholino, 4-$C_{1-6}$ alkylpiperidino, pyrrolidino, hexamethyleneimino or tetrahydropyridino;

Alk represents methylene;

Q represents a benzene ring incorporated into the rest of the molecule through bonds at the 1- and 3-positions; or a furan ring incorporated into the rest of the molecule through bonds at the 2- and 5-positions optionally bearing a substituent $R_4$ adjacent to the group $R_1R_2NAlk$ where $R_4$ is $C_{1-4}$ alkyl; or a thiophene ring incorporated into the rest of the molecule through bonds at the 2- and 4-positions with the substituent $R_1R_2NAlk$ in the 2-position; with the provisos that when Q is a benzene ring as just defined, then X is a bond, n is zero, Y is oxygen and m is 3, 4 or 5, or X and Y both represent oxygen and n and m are both 2, or X is oxygen, Y is CHOH and n and m are both 1; and when Q is a furan or thiophene ring as just defined, then X is a bond and either Y is sulphur or $CH_2$, n is 1 and m is 2, or Y is oxygen, n is 1 and m is 3;

$R_3$ represents hydrogen or $C_{1-6}$ alkyl;

$R_5$ represents a $C_{2-4}$ alkyl group substituted by two hydroxy groups, or a 2,2-di $C_{1-3}$ alkyl-1,3-dioxolan-4-yl group; or $R_5$ represents the group $(CH_2)_qZ(CH_2)_rR_8$, in which q is 1, r is 1 to 4 when Z is oxygen or r is 1 when Z is sulphur, and $R_8$ is hydroxy, the group $-CH=CH_2$, di $C_{1-3}$ alkylamino, or the group $COR_9$ where $R_9$ is $C_{1-4}$ alkoxy or the group $NHR_{11}$ where $R_{11}$ is $C_{1-3}$ alkyl; or $R_5$ represents the group $(CH_2)_xS(CH_2)_yR_{15}$ in which X represents 1 and the heteroaryl group $R_{15}$ is tetrazolyl or thiadiazolyl each of which is substituted by $C_{1-3}$ alkyl, or $R_{15}$ is furyl.

3. A compound as claimed in claim 2, wherein $R_1R_2N$ represents piperidino, morpholino, 4-$C_{1-6}$ alkylpiperidino, pyrrolidino, hexamethylinimino or tetrahydropyridino.

4. A compound having a formula (II)

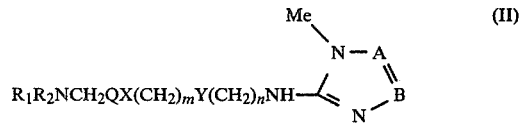

or a physiologically acceptable salt or hydrate thereof in which $R_1R_2N$ represents di $C_{1-3}$ alkylamino, furylmethylamino, or pyrrolidino, piperidino, 4-methylpiperidino, tetrahydropyridino or hexamethylenimino;

A represents N and B represents $CR_5$, or A represents $CR_5$ and B represents N, where $R_5$ represents $C_{2-4}$ alkyl substituted by two hydroxy groups, 2,2-di $C_{1-3}$ alkyl-1,3-dioxolan-4-yl, (1-methyl-1H-tetrazol-5-yl)thiomethyl, or $R_5$ represents the group $CH_2Z(CH_2)_rR_8$ where $R_8$ is hydroxy or di $C_{1-3}$ alkylamino, Z is oxygen and r is 4; or $R_8$ is the group $-CH=CH_2$ or the group $COR_9$ where $R_9$ is $C_{1-4}$ alkoxy, Z is oxygen or sulphur and r is 1; and either Q is 1,3-benzene and X is a bond, n is zero, Y is oxygen and m is 3 or 4; or X is oxygen, n is 1, Y is —CHOH— and m is 1;

or Q is 2,5-furan or 2,4-thiophene, X is a bond, Y is sulphur, n is 1 and m is 2; with the proviso that $R_1R_2N$ is di $C_{1-3}$ alkylamino when Q is a furan or thiophene ring.

5. A compound as claimed in claim 1 which is selected from:
1-methyl-3-[[(1-methyl-1H-tetrazol-5-yl)thio]methyl]-N-[3-[3-(1-piperidinylmethyl)phenoxy]propyl]-1H-1,2,4-triazol-5-amine
and physiologically acceptable salts thereof.

6. A compound as claimed in claim 1 which is selected from:
1-methyl-5-[3-[[(1-piperidinylmethyl)phenoxy]propyl]amino]-1H-1,2,4-triazole-3-ethane-1,2-diol
and physiologically acceptable salts thereof.

7. A pharmaceutical composition for the treatment of conditions mediated through $H_2$-receptors comprising an effective amount of a compound of formula (I) as defined in claim 1 together with at least one pharmaceutically acceptable carrier or diluent.

8. A method of treating a condition mediated through $H_2$-receptors which comprises administering to a patient an effective amount of a compound according to claim 1 to relieve said condition.

* * * * *